(12) United States Patent
Bonning et al.

(10) Patent No.: US 7,547,677 B2
(45) Date of Patent: Jun. 16, 2009

(54) PLANT VIRUS TRANSMISSION INHIBITOR AND METHODS

(75) Inventors: Bryony Bonning, Ames, IA (US); W. Allen Miller, Ames, IA (US); Sijun Liu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 12/001,776

(22) Filed: Dec. 11, 2007

(65) Prior Publication Data

US 2009/0055975 A1    Feb. 26, 2009

Related U.S. Application Data

(60) Provisional application No. 60/869,545, filed on Dec. 11, 2006.

(51) Int. Cl.
*A61K 38/10* (2006.01)
*C07K 7/08* (2006.01)
*C12P 21/06* (2006.01)
*A01H 1/00* (2006.01)
*C12N 15/11* (2006.01)

(52) U.S. Cl. .......................... 514/14; 435/69.1; 800/295; 800/302; 530/327

(58) Field of Classification Search ........................ None
See application file for complete search history.

(56) References Cited

U.S. PATENT DOCUMENTS

| | | |
|---|---|---|
| 5,866,363 A | 2/1999 | Pieczenik |
| 6,605,448 B1 | 8/2003 | Pieczenik |
| 7,312,080 B2 | 12/2007 | Miller et al. |

FOREIGN PATENT DOCUMENTS

WO    WO 00/66755    11/2000

OTHER PUBLICATIONS

Baulcombe, D.C. (Oct. 1996) "Mechanisms of Pathogen-Derived Resistance to Viruses in Transgenic Plants," *Plant Cell* 8:1833-1844.
Booker et al. (Feb. 2003) "Auxin Acts in Xylem-Associated or Medullary Cells to mediate Apical Dominance," *Plant Cell* 15(2):495-507.
Brault et al. (Aug. 2005) "The Polerovirus Minor Capsid Protein Determines Vector Specificity and Intestinal Tropism in the Aphid," *J. Virol.* 79(15):9685-9693.
Chay et al. (1996) "Aphid Transmission and Systemic Plant Infection Determinants of Barley Yellow Dwarf Luteovirus-PAV are Contained in the Coat Protein Readthrough Domain and 17-kDa Protein, Respectively, " *Virology* 219:57-65.
Chowrira et al. (1998) "Coat Protein-Mediated Resistance to Pea Enation Mosaic Virus in Transgenic *Pisum sativum* L.," *Trans. Res.* 7:265-271.
Demler et al. (1997) "Expression and Suppression of Circulative Aphid Transmission in Pea Enation Mosaic Virus," *J. Gen. Virol.* 78:511-523.
Demler et al. (1994) "Assessment of the Automomy of Replicative and Structural Functions Encoded by the Luteo-Phase of Pea Enation Mosaic Virus," *J. Gen. Virol.* 75(5):997-1007.
Devlin et al. (Jul. 27, 1990) "Random Peptide Libraries: A Source of Specific Protein Binding Molecules," *Science* 249:404-406.
Fitchen et al. (1993) "Genetically Engineered Protection Against Viruses in Transgenic Plants," *Ann. Rev. Microbiol.* 47:739-763.
Garret et al. (1993) "The Intestine is a Site of Passage for Potato Leafroll Virus from the Gut Lumen into the Hemocoel in the Aphid Vector, *Myzus persicae* Sulz.," *Arch. Virol.* 131:377-392.
GeneBank Accession No. Y09099, "Pea Enation Mosaic Virus Genes Encoding 21 kDa Coat Protein and 54 kDa Readthrough Protein, Aphid Transmissible Isolate," Demler et al. (1996).
GeneBank Accession No. AY661882, "Pea Enation Mosaic Virus Isolate UP 58 Coat Protein Gene, Complete cds," Navratil et al. (2004).
Ghosh et al. (2001) "Targeting *Plasmodium* Ligands on Mosquito Salivary Glands and Midgut with a Phage Display Peptide Library," *Proc. Nat. Acad. Sci. USA* 98(23):13278-13281.
Gildow et al. (1993) "The Aphid Salivary Gland Basal Lamina as a Selective Barrier Associated with Vector-Specific Transmission of Barley Yellow Dwarf Luteoviruses," *Phytopathology* 83(12):1293-1302.
Gildow et al, (1993) "Evidence for Receptor-Mediating Endocytosis Regulating Luteovirus Acquisition by Aphids," *Phytopathology* 83(3):270-277.
Gildow et al. (1993) "Luteovirus Transmission and Mechanisms Regulating Vector Specificity," In; *The Luteoviridae*, Smith et al. Eds., Wallingford, UK, CABI Publishing, pp. 88-113.
Gildow, F.E. (1982) "Coated Vesicle Transport of Luteovirus Through the Salivary Gland of *Myzus persicae,*" *Phytopathology* 72:1289-1296.
Gildow et al. (2000) "Aphid Acquisition and Cellular Transport of Potato Leafroll Virus-Like Particles lacking P5 Readthrough Protein," *Phytopathology* 90:1153-1161.
Gold Bach et al. (2003) "Resistance Mechanisms to Plant Viruses: An Overview," *Virus Res.* 92:207-212.
Gray, S.M. (Jul. 1996) "Plant Virus Proteins Involved in Natural Vector Transmission," *Trends Microbiol.* 4(7):259-264.
Gray et al. (2003) "Luteovirus-Aphid Interactions," *Ann. Rev. Phytopathol.* 41:539-566.
Hewings et al. (1995) "Epidemiology of Barley Yellow Dwarf in North America," In; *Barley Yellow Dwarf: 40 Years of Progress*, D'Arcy et al. Eds., St. Paul, APS Press, pp. 75-106.

(Continued)

*Primary Examiner*—Andrew D Kosar
(74) *Attorney, Agent, or Firm*—Greenlee, Winner and Sullivan, P.C.

(57) ABSTRACT

Provided is a peptide, peptide multimer or fusion protein containing such peptide which binds to the gut of sap-sucking insects, e.g., aphids. When bound, this peptide inhibits the binding of targeted virus to the insect gut. When this peptide or tandem repeat peptide is expressed (or is expressed as part of a fusion protein) in the fluids of transgenic plants, it is taken up by the insect with the sap, binds to gut receptors and thereby inhibits transmission of the virus from plant to plant via the insect vector. Thus, the use of such transgenic plants blocks or reduces the transmission of the targeted virus and others which share the peptide binding site within the insect gut among plants susceptible to the virus and thereby reduces losses due to viral infection.

16 Claims, 6 Drawing Sheets

OTHER PUBLICATIONS

Jacobs-Lorena, M. (2003) "Interrupting Malaria Transmission by Genetic Manipulation of Anopheline Mosquitoes," *J. Vector Borne. Dis.* 40:73-77.

James, A.A. (2003) "Blocking Malaria Parasite Invasion of Mosquito Salivary Glands," *J. Exp. Biol.* 206:3817-3821.

Jones et al. (Nov. 1992) "Effective Vectors for Transformation, Expression of Heterologous Genes, and Assaying Transposon Excision in Transgenic Plants," *Transgenic Res.* 1(6):285-297.

Jordan et al. (Apr. 1993) "Evaluation of a Cotyledonary Node Regeneration System for *Agrobacterium*-Mediated Transformation of PEA (*Pisum sativum* L.)," In Vitro *Cell Dev. Biol.* 29:77-82.

Koec et al. (1998) "Extreme Reduction of Disease in Oats Transformed with the 5' half of the Barley Yellow Dwarf Virus-PAV Genome," *Phytopathology* 88:1013-1019.

Koev et al. (Jan. 5, 2002) "The 3'-Terminal Structure Required for Replication of Barley Yellow Dwarf Virus RNA Contains an Embedded 3' End," *Virology* 292(1):114-126.

Krejčí et al, (2007) "The Transformation of Pea (*Pisum sativum* L.): Applicable Methods of *Agrobacterium tumfaciens*-Mediated Gene Transfer," *Acta Physiol. Plant.* 29:157-163.

Liu et al. (Dec. 11, 2006) "A Short Peptide Competes with *Pea enation mosaic virus* for Binding to the Gut of the Pea Aphid, *Acrythosiphon pisum*," Poster Presented through the Entomological Society of America, Dec. 11, 2006.

Liu et al. (2006) "A Simple Wax-Embedded Method for Isolation of Aphid Hemolymph for Detection of Luteoviruses in the Hemocoel," *J. Virol. Methods*.

Marcos et al. (Feb. 1994) "In Vitro Characterization of a Cassette to Accumulate Multiple Proteins Through Synthesis of a Self-Processing Polypeptide," *Plant Mol. Biol.* 24(3):495-503.

Mehlo et al. (May 31, 2005) "An Alternative Strategy for Sustainable Pest Resistance in Genetically Enhanced Crops," *Proc. Nat. Acad. Sci. USA* 102(22):7812-7816.

Miles, P.W. (1989) "Specific Responses and Damage Caused by *Aphidoidea*," In; *Aphids. Their Biology, Natural Enemies and Control*, Minks et al. Eds., Amsterdam, Elsevier. C: pp. 23-47.

Miller et al. (1997) "Are There Risks Associated with Transgenic Resistance to Luteoviruses," *Plant. Dis.* 81(7):700-710.

Nauerby et al. (Apr. 1991) "A Rapid and Efficient Regeneration System for Pea (*Pisum sativum*), Suitable for Transformation," *Plant Cell Reports* 9(12):676-679.

Reinbold et al. (2003) "Posterior Midgut and Hindgut are Both Sites of Acquisition of Cucurbit Aphid-Borne Yellows Virus in *Myzus persicae* and *Aphis gossypii*," *J. Gen. Virol.* 84:3473-3484.

Rouze-Jouan et al. (2001) "The Passage of Potato Leafroll Virus Through *Myzus persicae* Gut Membrane Regulated Transmission Efficiency," *J. Gen. Virol.* 82:17-23.

Scholthof et al. (1993) "Control of Plant Virus Diseases by Pathogen Derived Resistance in Transgenic Plants," *Plant Physiol.* 102:7-12.

Scott et al. (Jul. 27, 1990) "Searching for Peptide Ligands with an Epitope Library." *Science* 249:386390.

Seddas et al. (2004) "Rack-1, GAPDH3, and Actin: Proteins of *Myzus persicae* Potentially Involved in the Transcytosis of Beet Western Yellows Virus Particles in the Aphid," *Virology* 325:399-412.

Smith et al. (1993) "Libraries of Peptides and Proteins Displayed on Filamentous Phage," *Methods Enzymol.* 217:228-257.

Smith, G.P. (Jun. 14, 1985) "Filamentous Fusion Phage: Novel Expression Vectors that Display Cloned Antigen on the Virion Surface," *Science* 228:1315-1317.

Sylvester, E.S. (1989) "Viruses Transmitted by Aphids," In; *Aphids. Their Biology, Natural Enemies and Control*, Minks et al. Eds., Amsterdam, Elsevier. C: pp. 65-88.

Tepfer, M. (2002) "Risk Assessment of Virus-Resistant Transgenic Plants," *Ann. Rev. Phytopathol.* 40:467-491.

Terradot et al. (Jul. 20, 2001) "Analysis of a Three-Dimensional Structure of *Potato leafroll virus* Coat Protein Obtained by Homology Modeling," *Virology* 286(1)72-82.

Thomas et al. (2000) "Extreme Resistance to Potato Leafroll Virus in Potato cv. Russet Burbank Mediated by the Viral Replicase Gene," *Virus Res.* 71:49-62.

Torrance, L. (1992) "Analysis of Epitopes on Potato Leafroll Virus Capsid Protein," *Virology* 191(2):485-489.

Truenit et al. (Jun. 1995) "The Promoter of the *Arabidopsis thaliana* SUC2 Sucrose-H+ Symporter Gene Directs Expression of β-Glucuronidase to the Phloem: Evidence for Phloem Loading and Unloading by SUC2," *Planta* 196(3):564-570.

von Bodman et al. (Jun. 13, 1995) ,,Expression of Multiple Eukaryotic Genes from a Single Promoter in *Nicotiana, BioTechnology* 13:587-591.

Wilson, T.M.A. (Apr. 1993) "Strategies to Protect Crop Plants against Viruses: Pathogen-Derived Resistance Blossoms," *Proc. Nat. Acad. Sci. USA* 90:3134-3141.

Xiang et al. (Jul. 1999) "A Mini Binary Vector Series for Plant Transformation," *Plant. Mol. Biol.* 40(4):711-717.

|  | A | T | C | S | K | K | Y | P | R | S | P | C | M | A |  |
|---|---|---|---|---|---|---|---|---|---|---|---|---|---|---|---|
| 4 | R | S | R | S | K | A | N | Q | R | R | R | P | R |  | 17 |
| 9 | A | N | Q | R | R | R | R | P | R | R | V | V | V | v | 22 |
| 14 | R | R | P | R | R | V | V | V | V | A | P | S | M | A | 27 |
| 22 | V | A | P | S | M | A | Q | P | R | T | Q | S | R | R | 35 |
| 30 | R | T | Q | S | R | R | P | R | R | R | N | K | R | G | 44 |
| 65 | A | T | G | T | V | K | F | G | P | S | S | D | C | Q | 78 |
| 66 | T | G | T | V | K | F | G | P | S | S | D | C | Q | C | 79 |
| 92 | I | V | W | L | K | V | V | Y | Q | S | E | A | A | A | 105 |
| 127 | V | L | L | D | T | W | N | I | R | S | N | G | S | A | 140

PLANT VIRUS TRANSMISSION INHIBITOR AND METHODS

CROSS REFERENCE TO RELATED APPLICATIONS

This application claims benefit of U.S. Provisional Application 60/869,545, filed Dec. 11, 2006, which application is incorporated by reference herein to the extent there is no inconsistency with the present application.

ACKNOWLEDGEMENT OF FEDERAL RESEARCH FUNDING

Not applicable.

REFERENCE TO SEQUENCE LISTING

The Sequence Listing filed on even date herewith is incorporated by reference herein.

BACKGROUND OF THE INVENTION

Members of the Luteoviridae, such as Barley yellow dwarf virus (BYDV), Potato leaf roll virus (PLRV) and Beet western yellows virus (BWYV) are crop pathogens of global economic importance (Sylvester, E. S. 1989. A. K. Minks and P. Harrewiojn, Amsterdam, Elsevier. C:65-88; Blackman, R. L. 2000. An identification and information guide. New York, John Wiley and Sons). During aphid feeding, the virions of such plant viruses that are transmitted in a persistent or circulative manner, pass with the sap through the maxillary food canal of the aphid stylet into the gut. From the gut (midgut or hindgut) the virions penetrate the gut epithelium by endocytosis (Gildow, F. E. et al. 1993. *Phytopathology* 83:1293-1302; Gray, S. M. 1996. *Trends Microbiol.* 4(7):259-264) (FIG. 1). The virus-containing vesicle fuses with the plasmalemma, thereby releasing the virus, which readily passes through the basement membrane into the hemocoel. The virus is then transported to the accessory salivary gland (ASG). Upon aphid feeding, the luteovirus is injected into the plant with saliva via the salivary canal in the maxillary stylets (FIG. 1).

The transmission of plant viruses involves specific molecular interactions between the virus and its vector: For aphid transmission of luteoviruses, the virus must bind to a receptor in the gut for uptake into the hemocoel, where the virus circulates. A second receptor is involved in movement of virus from the hemocoel into the accessory salivary gland (ASG), from which the virus is delivered with the aphid saliva into the phloem of the plant. Despite several attempts, no aphid receptor involved in plant virus—aphid interaction has been identified.

There is a long felt need in the art for environmentally friendly and economical methods for reducing damage to both crop and ornamental plants from virus infection. The present invention meets this need.

SUMMARY OF THE INVENTION

There is provided a peptide that specifically inhibits binding of a targeted plant virus to a receptor in an insect gut. Also provided are peptide multimers and fusion proteins incorporating this peptide sequence, for example as an N-terminal extension of a protein. By preventing the gut binding of the targeted virus acquired by the insect feeding on an infected plant, the peptide provided herein or the fusion protein incorporating said peptide interferes with insect transmission of the virus to uninfected plants. The use of this peptide applies to insects which feed on plant fluids, including but not limited to, aphids and planthoppers, whiteflies (Hemiptera) and thrips (Thysanoptera). Virus-susceptible plants can be transformed to express a peptide of the invention in the plant phloem, upon which insects such as aphids feed. An aphid feeding on the phloem of a transgenic plant expressing a peptide (or fusion protein incorporating same) provided herein thereby acquires the peptide in its gut, where the peptide inhibits binding of any targeted virus acquired, such that the cycle of virus transmission by the aphid is interrupted. Transgenic plants expressing the peptide, a peptide multimer or fusion protein including this peptide inhibit plant-to-plant transmission of any virus for which the peptide is targeted, lower the incidence of virus infection in a crop of such plants and thereby reduce viral damage by the targeted virus in the crop as a whole.

Peptides of the invention include the following:

```
a Thr Cys Ser Lys Lys Tyr Pro Arg Ser Pro Cys Met Ala     (SEQ ID NO: 1)

Ala Thr Cys Ser Lys Lys Tyr Pro Ser Ser Asp Cys Gln Ala   (SEQ ID NO: 2)

Ala Thr Cys Ser Lys Lys Tyr Pro Ser Ser Glu Cys Met Ala   (SEQ ID NO: 3)

Ala Thr Cys Ser Lys Lys Tyr Pro Arg Ser Asp Cys Met Ala   (SEQ ID NO: 4)

Ala Thr Cys Ser Lys Lys Tyr Pro Ser Ser Pro Cys Gln Ala   (SEQ ID NO: 5)

Ala Thr Cys Ser Lys Lys Tyr Pro Arg Ser Pro Cys Gln Ala   (SEQ ID NO: 6)

Ala Gly Cys Ser Lys Lys Tyr Pro Arg Ser Pro Cys Met Ala   (SEQ ID NO: 7)
```

The N- and C-terminal alanine residues of SEQ ID NOs: 1-7 are not required for inhibitory activity. Therefore the peptides of the invention also include

```
Thr Cys Ser Lys Lys Tyr Pro Arg Ser Pro Cys Met   (SEQ ID NO: 9)

Thr Cys Ser Lys Lys Tyr Pro Ser Ser Asp Cys Gln   (SEQ ID NO: 10)
```

-continued

Thr Cys Ser Lys Lys Tyr Pro Ser Ser Glu Cys Met (SEQ ID NO: 11)

Thr Cys Ser Lys Lys Tyr Pro Arg Ser Asp Cys Met (SEQ ID NO: 12)

Thr Cys Ser Lys Lys Tyr Pro Ser Ser Pro Cys Gln (SEQ ID NO: 13)

Thr Cys Ser Lys Lys Tyr Pro Arg Ser Pro Cys Gln (SEQ ID NO: 14)

Gly Cys Ser Lys Lys Tyr Pro Arg Ser Pro Cys Met (SEQ ID NO: 15)

The sequence of the gut-binding peptide provided herein can be expressed in terms of the following consensus sequence: $Xaa_1$-$Xaa_2$-Cys-Ser-Lys-Lys-Tyr-Pro-$Xaa_3$-Ser-$Xaa_4$-Cys-$Xaa_5$-$Xaa_6$, wherein $Xaa_1$ and $Xaa_6$, independently of one another, can be any amino acid or no amino acid; $Xaa_2$ is Thr or Gly; $Xaa_3$ is Arg or Ser; $Xaa_4$ is Asp or Glu or Pro; and $Xaa_5$ is Met or Gln (SEQ ID NO:29). A nucleotide sequence encoding an amino acid sequence corresponding to this consensus sequence can be incorporated into the coding sequence of a protein to form a fusion protein, especially where it is incorporated at the N-terminus of the protein (preceded by a Met residue to initiate transcription or where the recited sequence of amino acids is preceded by a signal peptide to allow secretion of the gut-binding fusion protein into the sap of a transgenic plant expressing same). Alternatively, such a peptide can be expressed as a peptide multimer (of identical peptide or one or more peptides of sequences fitting the consensus sequence of SEQ ID NO:29).

The gut-binding peptides, peptide multimer and fusion proteins containing same provided herein are especially useful for inhibiting the binding of Pea enation mosaic virus (PEMV) to an aphid gut, and to prevent transfer of the PEMV into the aphid hemocoel. As a result, aphid-to-plant transmission of this virus is inhibited, and thus the incidence and transmission of viral infection in susceptible plants is reduced. Of particular interest are those plants which are susceptible to luteoviruses and enamoviruses, especially PEMV; these include, without limitation, garden, field and sweet peas, broad beans and sweet clover, *Chenopodium album, Chenopodium amaranticolor, Chenopodium quinoa, Cicer arietinum, Lathyrus odoratus, Lens culinaris, Lespedeza stipulacea, Lupinus albus, Lupinus angustifolius, Medicago arabica, Medicago sativa* (alfalfa), *Melilotus albus, Nicotiana clevelandii, Phaseolus vulgaris, Pisum sativum, Trifolium hybridum, Trifolium incarnatum, Trifolium repens, Trifolium subterraneum, Vicia faba, Vicia sativa* and *Vicia villosa*. PEMV is also transmitted by the peach green aphid *Myzus persicae*; the gut-binding peptide and its fusion proteins also inhibit transmission of the virus by this insect pest.

A DNA sequence encoding the peptide of SEQ ID NO:1 lacking the N-terminal and C-terminal alanine residues is ACG TGT AGT AAG MG TAT CCG CGT TCT CCG TGT ATG (SEQ ID NO:17). It is understood that other synonymous coding sequences can be substituted for SEQ ID NO: 17 in the practice of various embodiments of the present invention.

A further embodiment of the invention encompasses a method of inhibiting entry of a target virus ingested by an insects including aphids, planthoppers, thrips or whiteflies into the hemocoel of the insect, comprising providing a peptide, peptide multimer or fusion protein comprising the amino acid sequence of the peptide set forth in the consensus sequence set forth in SEQ ID NO:29 that inhibits binding of the virus to the insect gut, and bringing a source of food containing the peptide multimer or fusion protein into contact with the insect under conditions that allow the insect to ingest the food, whereby the peptide ingested by the insect inhibits entry of any target virus ingested by the insect into the hemocoel of the insect. As a result transmission of the target virus to a susceptible plant is reduced, and incidence and/or severity of disease caused by the virus is reduced. The peptides, peptide multimers and fusion proteins provided herein inhibit binding of Luteoviruses, Geminiviruses and Enamoviruses, in particular Pea enation mosaic virus (PEMV), to the aphid gut. Virus binding to the guts of other sap-sucking insects is also inhibited.

DESCRIPTION OF THE DRAWINGS

FIG. 2 provides sequence alignment of the amino acid sequence of peptide GBP3.1 displayed by PhD3.1 (SEQ ID NO:1) (top sequence) with fragments of PEMV coat protein that have at least 3 amino acids matching with the PhD3.1-displayed sequence. The numbers to the left and right of the PEMV segments are the amino acid positions in the coat protein sequence. The top sequence is that of SEQ ID NO:1; amino acids 4-17 correspond to SEQ ID NO:30; amino acids 9-22 correspond to SEQ ID NO:31; amino acids 14-27 correspond to SEQ ID NO:32; amino acids 22-35 correspond to SEQ ID NO:33; amino acids correspond to SEQ ID NO:33; amino acids 30-44 correspond to SEQ ID NO:34; amino acids 65-78 correspond to SEQ ID NO:35; amino acids 66-79 correspond to SEQ ID NO:36; amino acids 92-105 correspond to SEQ ID NO:37; and amino acids 127-140 correspond to SEQ ID NO:38.

DETAILED DESCRIPTION OF THE INVENTION

Figure 1A:
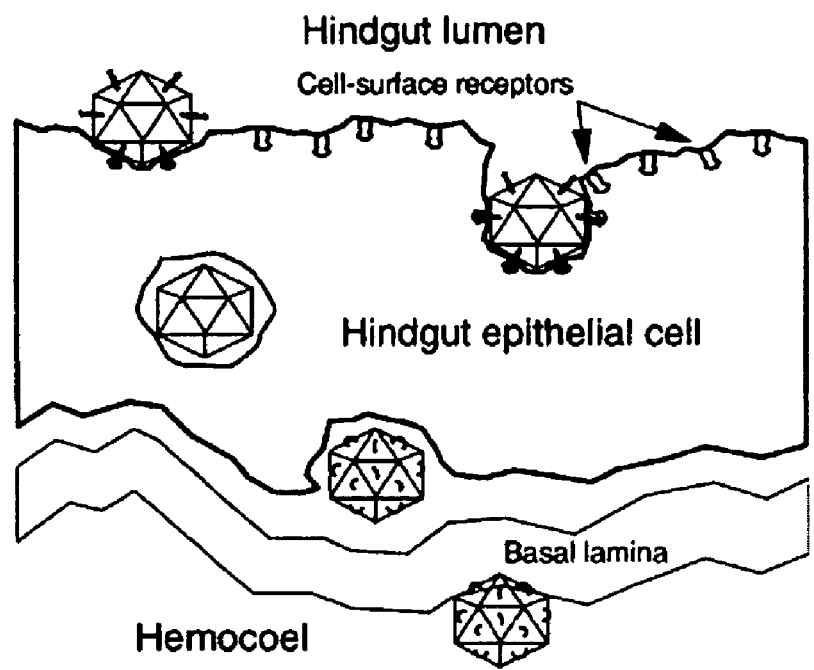
FIG. 1A is a diagram of the mechanism of receptor-mediated endocytosis of luteoviruses from the hindgut into the aphid hemocoel (Gray, supra). The virus binds to specific receptors on the epithelial cells of the hindgut and is taken up by endocytosis. The virus-containing vesicle then fuses with the basal plasmalemma of the epithelial cell, thereby releasing the virus, which then readily moves through the basal laminar (basement membrane) into the hemolymph.
Figure 1B:
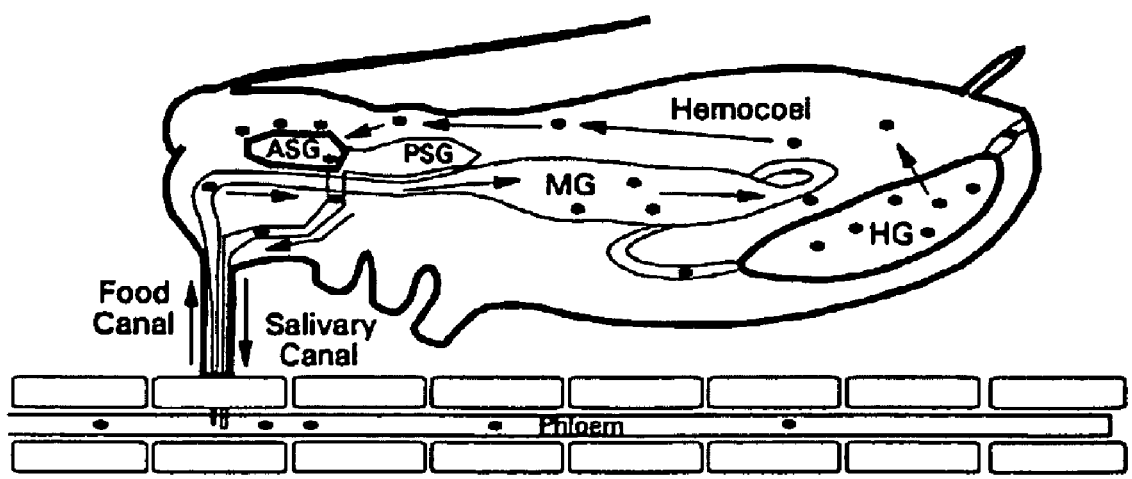
FIG. 1B is a diagram representing an aphid in saggital section to illustrate circulative luteovirus transmission (Gildow, supra; Chay, C. A. et al. 1996. *Virology* 219:57-65). HG, hindgut; MG, midgut; ASG, accessory salivary gland; PSG, primary salivary gland.

The term "inhibit" is used in the art-recognized meaning to indicate a reduction in rate or amount of a measurable interaction. A peptide or fusion protein comprising same of the present invention inhibits transfer of insect-ingested virus to hemocoel of an insect, as measured by a block or delay in presence of detectable virus RNA in the insect hemocoel after feeding on virus-infected plants. See Example 3 herein below. Without wishing to be bound by theory, the inventors believe that the peptide competes with or blocks binding of the target virus for binding with a receptor in the insect gut.

The term "fusion protein" is used herein to describe a protein comprising portions from different sources (not both parts of the same naturally occurring polypeptide chain). Optionally a linker region may be included to facilitate folding of the domains (portions) into their natural conformations by reducing steric hindrance between those domains. Such a fusion protein may have an additional domain, for example a tag sequence to facilitate purification of the fusion protein. A tag can be any of a number of known tags widely known and available to the art (Streptavidin-binding, glutathione binding, polyhistidine, flagellar antigen and others).

The term "transmit" is used herein in the context of virus infection. An insect transmits a virus to a plant by causing transfer of virus from insect to plant. The insect acts as a vector for infection by the virus, by transmitting the virus from insect to plant.

In the present context, the term "peptide" does not encompass the full-length protein from which the peptide's sequence was derived. However, in the context of the present disclosure, the term peptide encompasses a single peptide of 3 to 14 amino acids as well as an oligopeptide or polypeptide made up of repeats of identical or nonidentical amino acid sequences, each of which fits the consensus sequence of SEQ ID NO:29 or core amino acid sequences shared by various segments of the PEMV coat protein or other virus coat proteins.

The results described herein exemplify an embodiment of the invention, the peptide displayed by phage PhD3.1. SEQ ID NO:1 provides the sequence of the PhD3.1-displayed peptide having N- and C-terminal alanine residues. However, the N- and C-terminal alanine residues are not required for functional activity of the peptide displayed by PhD3.1. The Examples demonstrate inhibition by PhD3.1 of PEMV binding to aphid gut tissue. The method described herein for identifying PhD3.1 and demonstrating its activity are readily applied to isolating and characterizing other peptides that inhibit the binding of other circulatively transmitted plant viruses. Such viruses include, but are not limited to: Luteoviruses, Geminiviruses and any other viruses transmitted in a circulative, persistent fashion by insects within the order Hemiptera, which includes aphids and planthoppers, and white flies (Hemiptera), and thrips (order Thysanoptera). Luteoviruses of significant economic importance include members of the genus *Luteovirus* (Barley yellow dwarf virus, Soybean dwarf virus), the genus *Polerovirus* (Potato Leaf Roll virus (PLRV) and Beet western yellow virus), and the genus *Enamovirus* (pea enation mosaic virus (PEMV). Particularly relevant insects are aphids, species of which include *Rhopalosiphum padi, Sitobion avenae, Microsiphum avenae, Schizaphis graminum*, and *Acyrthosiphon pisum* and *Myzus persicae*.

Plants susceptible to PEMV (among other related and relevant viruses) include, without limitation, *Chenopodium album, Chenopodium amaranticolor, Chenopodium quinoa, Cicer arietinum, Lathyrus odoratus, Lens culinaris, Lespedeza stipulacea, Lupinus albus, Lupinus angustifolius, Medicago Arabica, Medicago sativa, Melilotus albus, Nicotiana clevelandii, Phaseolus vulgaris, Pisum sativum, Trifolium hybridum, Trifolium incarnatum, Trifolium repens, Trifolium subterraneum, Vicia faba, Vicia sativa* and *Vicia villosa*. Expression of a peptide or fusion protein of the invention in these plants will lessen the spread of viral disease among these plants and thereby reduce losses due to such viral infection The choice of insect vector depends on the virus to be inhibited, as understood in the art. Techniques described herein that were developed for experimental studies of the aphid species used in the example can also be applied to other aphid species and to other insect vectors, especially sap-sucking insects, such as thrips, aphids, leafhoppers and white-flies, of circulatively transmitted viruses.

EXAMPLES

Example 1

Aphids and viruses. The pea aphid (*Acyrthosiphon pisum*), the primary vector of Pea enation mosaic virus (PEMV) was used for these experiments. *Acyrthosiphon pisum* were reared on pea (22-24° C., L; D 12:12 hrs). PEMV clones were generously provided by Dr. G. A. de Zoeten. The phage display library (derived from phage f88.4) was provided by Dr. Jamie Scott, Simon Fraser University, Canada (Smith, G. P. and Scott, J. K. (1993) Methods in Enzymology 217:228-257). Phage were cultured in *Escherichia coli* K-91. The library was cultured, amplified, purified and titered using standard procedures.

Membrane feeding of aphids with phage. To optimize feeding of aphids on solutions of phage, aphids were held without food overnight at 4° C. and then fed through Parafilm membranes on phage in a 25% sucrose and 10-15% glycerol solution. This protocol greatly improved feeding efficiency over previous methods and can also facilitate membrane feeding with plant viruses.

Isolation of aphid guts. A wax-embedding method developed to trap aphids for isolation of aphid hemolymph (blood) (Liu, S. et al. (2006) *J. Virol. Methods* 132 (102):174-180)

was modified for isolation of aphid guts. Aphids were embedded in black wax, and covered with PBS buffer prior to dissection using a binocular microscope. The black background facilitated visualization and identification of the gut. Guts were isolated and transferred to eppendorf tubes.

Elution of bound phage. Because of the small size of aphid guts, it was not possible to cut them open to wash out unbound phage, and then elute bound phage as described previously for mosquitoes (Ghosh, A. K. et al. (2001) *Proc Natl. Acad. Sci. USA* 98:13278-13281; Jacobs-Lorena, M. (2003) *J Vector Borne Dis.* 40:73-77; James, A. A. (2003) *J. Experimental Biology* 206:3817-3821) Aphid guts were cut into small pieces with a sharp needle, and gently homogenized in a 1.5 ml tube. After two rounds of washing, bound phage were eluted by adding elution buffer. Eluted phage were titrated to estimate the number of phage bound to the aphid gut. Eluted phage were unstable in elution buffer and were immediately amplified for use in the next round of bio-panning.

Three rounds of bio-panning were conducted to select for phage that bound to the aphid gut epithelium. The whole procedure was replicated twice. A phage displaying the sequence given in SEQ ID NO:1 was isolated and named PhD3.1.

Peptide blocking of PEMV uptake. Aphids were fed on phage (PhD3.1 or control phage PhDC6) overnight by membrane feeding and then transferred to PEMV-infected plants. Control aphids were transferred directly to PEMV infected plants without prior treatment. Hemolymph was isolated from aphids at various times after onset of feeding on the plant, and tested, in groups of five from each treatment, for the presence of viral RNA by RT-PCR.

Example 2

Isolation of PhD3.1 by Bio-Panning

Bio-panning was conducted by feeding aphids with phage, isolation of aphid guts, washing for removal of unbound phage, and elution of phage bound to the gut epithelium. Eluted phage were amplified and used for the next round of bio-panning. After each round of bio-panning between 400 and 1000 phage were recovered from the aphid gut epithelium. After the third round of bio-panning, eluted phage were isolated and the DNA from each of 14 phage was extracted. The DNA sequences encoding the peptides displayed by each phage were determined. All 14 of the eluted phage, isolated after the third round of selection, encoded the same peptide sequence as PhD3.1 (SEQ ID NO:9). Replication of the whole experiment gave the same result. To confirm that the phage display library encoded diverse peptide sequences, 10 phage from the library along with 10 phage from each of the first and second rounds of eluted phage were sequenced. All 10 phage sequenced from the original library had different encoded peptide sequences. Of phage eluted from the first and second rounds, zero and four had the same sequence as PhD3.1, respectively. These results indicate that the peptide sequence (SEQ ID NO:9) displayed by PhD3.1 was selected from a diverse phage population during the three rounds of bio-panning.

Example 3

Mapping the PhD3.1 Sequence to a Potential Epitope on PEMV and Other Luteovirus Coat Proteins We analyzed the 12 amino acid insert in PhD3.1 to determine whether the peptide insert shares similarity with the PEMV coat protein (CP) amino acid sequence. Without wishing to be bound by any particular theory, it is believed that the peptide binds to the same receptor as that recognized by PEMV, and predicted that PEMV CP has a similar epitope sequence on the surface of the virion.

The sequence of PEMV CP was aligned with the 12 amino acid peptide sequence (SEQ ID NO:9, lacking N- and C-terminal alanine residues of SEQ ID NO:1). It is understood that at least three amino acids are required to form an epitope (region binding to the gut receptor protein) (Torrance et al. 1992. Virology 191:485-489). Hence, a CP fragment with three or more amino acids of a viral CP aligned with the PhD3.1 peptide sequence may form an epitope. The results of the sequence alignment are shown in FIG. 2. According to the above criteria, there are nine CP fragments that may form epitopes (FIG. 2). The top sequence is that of SEQ ID NO:1; amino acids 4-17 correspond to SEQ ID NO:30; amino acids 9-22 correspond to SEQ ID NO:31; amino acids 14-27 correspond to SEQ ID NO:32; amino acids 22-35 correspond to SEQ ID NO:33; amino acids correspond to SEQ ID NO:33; amino acids 30-44 correspond to SEQ ID NO:34; amino acids 65-78 correspond to SEQ ID NO:35; amino acids 66-79 correspond to SEQ ID NO:36; amino acids 92-105 correspond to SEQ ID NO:37; and amino acids 127-140 correspond to SEQ ID NO:38.

All nine CP fragments shown in FIG. 2 (SEQ ID NOs:30-38) may recognize receptors on the surface of the aphid gut epithelium, thereby mediating uptake of the virus into the aphid hemocoel. Without CP structural information, it is difficult to predict which of the sequences are exposed on the outside of the virion. However, an epitope in the CP of Potato leafroll virus (PLRV), which is recognized by a monoclonal antibody has been characterized (Torrance, L. 1992. *Virology* 191(1):485-489; Terradot et al. 2001. *Virology* 286(1):72-82). This epitope His Asp Ser Ser Glu Asp Gln (SEQ ID NO:18) was predicted to be on the surface of PLRV. There is a similar motif between amino acid positions 65-78 of CP: 72-Gly Pro Ser Ser Asp Cys Gln (SEQ ID NO:19) (FIG. 2). The core epitope amino acids in PLRV are Ser Ser Glu Asp Gln (SEQ ID NO:20), compared to Ser Ser Asp Cys Gln (SEQ ID NO:21) in PEMV.

These results suggest that the peptide expressed and displayed by PhD3.1 can bind to receptors that mediate PEMV uptake into the aphid hemocoel. This peptide can also be effective for blocking uptake of other plant viruses such as PLRV in other aphid or sap-sucking insect vectors that have similar gut receptor sites to that of the aphid.

Example 4

Binding Competition Between PEMV and PhD3.1

Binding of PhD3.1 to the PEMV receptor can block virus binding, thereby preventing movement of the virus into the hemocoel. We conducted experiments to test the effect of PhD3.1 on movement of PEMV into the hemocoel. Three sets of aphid tests were performed. The first set was to determine the minimum time required from onset of feeding on a virus infected plant, for detection of viral RNA in the aphid hemocoel. Aphids were allowed to feed on PEMV infected plants for 5, 10, 15, 20, 25, 30, 40, 50, or 60 minutes. Hemolymph was then isolated from the aphids, total RNA purified and RT-PCR carried out for detection of viral RNA. The second and third sets of aphids were first fed overnight with the PhD3.1 or control phage PhDC6 respectively, and then transferred to infected plants for acquisition of PEMV. Aphids were then tested for the presence of viral RNA in the hemolymph at various times after onset of feeding on the infected plants. The results are summarized in Table 1 and FIG. 3.

Figure 3A:
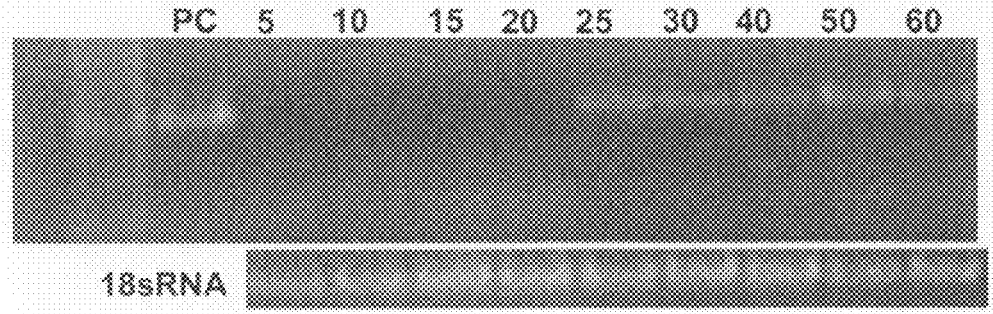
FIG. 3 shows the results of gel electrophoresis for detection of PEMV RNA molecules amplified by RT-PCR in aphid hemolymph for aphids fed on infected plants either without pretreatment (A) or following ingestion of phage expressing GBP3.1 (B) or the control peptide C6 (C). Numbers on the top of each gel indicate the duration of aphid feeding (minutes) on PEMV-infected plants. PC indicates a positive control. 18S indicates a sample of 18S RNA to control for loading to confirm that negative results were not caused by loss of RNA during the RNA extraction process.
Figure 3B:
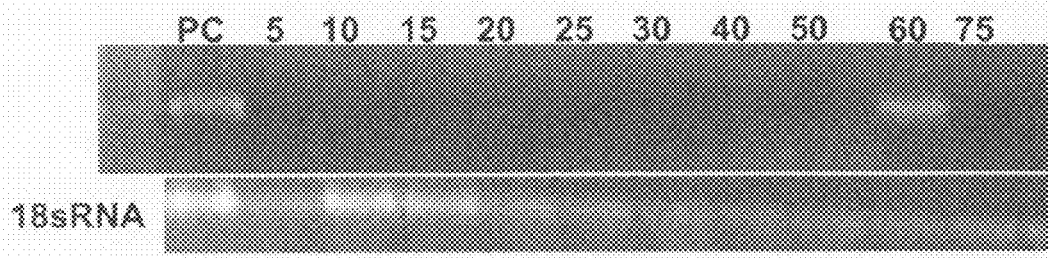
Figure 3C:
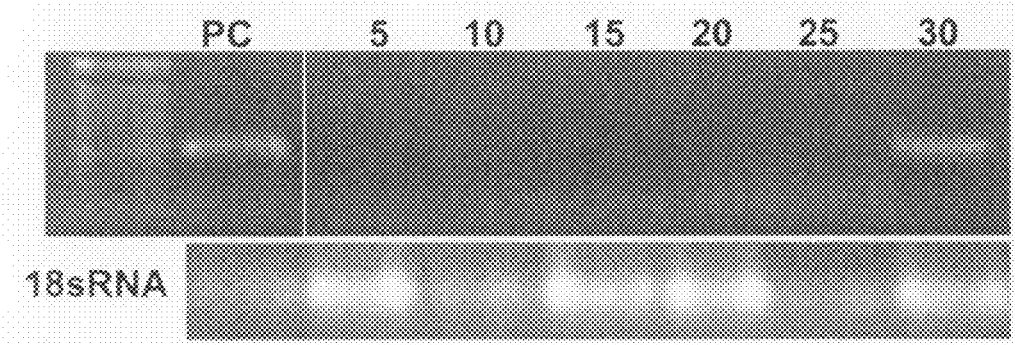

FIG. 3 shows detection of PEMV RNA in viruliferous aphid hemolymph, following ingestion of PhD3.1 or the phage displaying a control peptide. Numbers on the top indicate the duration of aphid feeding on PEMV infected plants (minutes). Each sample contained RNA from five aphids. PC is a positive control, which was prepared by purposefully damaging the aphid gut (of aphids fed on infected plants for 15 minutes) during hemolymph collection such that PEMV present in the aphid gut would be detected. FIG. 3A shows data for aphids fed on PEMV-infected plants. FIG. 3B shows data for aphids fed on PhD3.1 overnight before feeding on PEMV infected plants. FIG. 3C shows data for aphids fed on control phage PhDC6 overnight before feeding on PEMV-infected plants. The lower panels show 18S RNA to control for loading to confirm that negative results were not caused by loss of RNA during the RNA extraction process.

TABLE 1

Detection of PEMV RNA in the aphid hemocoel*

| | Time (min.) | | | | | | | |
|---|---|---|---|---|---|---|---|---|
| Treatment | 1-10 | 11-20 | 21-30 | 31-40 | 41-50 | 51-60 | 61-75 | 76-90 |
| Virus only | 0/6# | 0/8 | 6/12 (4/6) | 3/3 | 3/3 | 2/2 | 2/2 | 3/3 |
| PhD3.1 | 0/6 | 0/6 | 0/6 | 0/6 | 0/6 | 1/6 | 0/2 | 0/2 |
| Control phage | 0/4 | 0/4 | 2/4 | n/a | n/a | n/a | n/a | n/a |

*RNA in each sample was extracted from the hemolymph of five aphids: # No. of positive/No. of tested: Number in brackets is the result of aphid feeding for 30 minutes.

These data show that PhD3.1 inhibited movement of virus from the aphid gut to the hemocoel. For aphids fed on PEMV-infected plants, viral RNA could be detected in the hemolymph after 25 minutes (FIG. 3A). In contrast, for aphids fed first on PhD3.1, viral RNA was not detected until 60 minutes after onset of feeding on virus-infected plants. In some samples, viral RNA was not detected even after 90 minutes of feeding on virus-infected plants (Table 1). For aphids fed first on control phage, PEMV was detected in the hemolymph 30 minutes after virus acquisition (FIG. 3C), similar to the results for aphids fed on PEMV alone (FIG. 3A).

Without wishing to be bound by any particular theory, it is believed that ingested peptide may have been displaced during feeding on the infected plant, or insufficient peptide may have been ingested to block all receptor sites in these experiments and that when aphids continuously ingest peptide from a transgenic plant (rather than transiently feeding on peptide as described here), uptake of virus into the hemocoel is blocked.

A further competition was carried out in which the GBP3.1 sequence was expressed as part of an enhanced green fluorescent protein (EGFP) fusion protein. The GBP-GFP fusion protein was expressed in Escherichia coli. As a non-gut-binding control, the C6-EGFP fusion protein was also created and expressed in Escherichia coli. The amino acid sequence of the non-gut-binding control peptide "C6" is AFCRTAD-VIDACT (SEQ ID NO:22), and the nucleotide sequence encoding it is (SEQ ID NO: 23)
gcctttttgtcgtacggctgatgtgattgatgcgtgtac.

Construction of GBP3.1-EGFP and C6-EGFP Expression Vectors

The sequences encoding GBP3.1 and C6 sequences were cloned at the 5' end of the coding sequence for the EGFP, downstream of the His tag sequence and transcription start site (marker protein, enhanced green fluorescent protein) and cloned into the pBAD vector (Invitrogen).

Primers used for PCR cloning included forward primers GBP3.1-SacI (5'-CCG GAGCTCGgccacgtgtagtaagaagtatcc-3'; SEQ ID NO:24) and FGBP3.1-EGFP (5'-gccacgtgtagtaagaagtatccgcgt-tctccgtgtatggctgtgagcaagggcgagg-3'; SEQ ID NO:25) for GBP3.1-EGFP fusion and C6-SacI (5'-GCG GAGCTCGgcctttttgtcgtacggctgatgtg-3'; SEQ ID NO:26) and FC6-EGFP (5'-gcctttttgtcgtacggctgatgtgat-tgatgcgtgtacggctgtgagcaagggcgagg-3'; SEQ ID NO:27). Restriction sites underlined. The reverse primer is EGFP3'/Hind III (5'-CCAAAAGCTTGGttacttgtacagctcgtccatg-3'; SEQ ID NO:28). The template for PCR was pCPP-EGFP, a plasmid containing PEMV CP-EGFP fusion protein sequence.

The PCR was performed using a MyCycler Thermal Cycler (Bio-Rad Laboratories, Hercules, Calif.). High fidelity Pfu DNA polymerase (Stratagene, La Jolla, Calif.) was used for PCR according to the manufacturer's instructions. The PCR was conducted in 50 µl containing 25 pm GBP3.1/C6-SacI, 1 pm FGBP3.1/FC6-EGFP, 25 pm reverse primer, 50 ng PCPP-EGFP plasmid and 5 units of Pfu DNA polymerase. The polymerase chain reactions conditions were as follow: 1×94° C. for 2 mins; 5× of 94° C. for 45 s, 60° C. for 1.5 min., 72° C. for 4 mins.; 30× of 94° C. for 45 s, 60° C. for 35S, 72° C. for 4 mins and followed by 72° C. for 7 mins.

The PCR products were separated by electrophoresis in a 1% agarose gel and stained with ethidium bromide (EtBr). The DNA fragments of the correct size (0.78 Kb) were isolated and purified by using a QIAquick™ Gel Extraction Kit (Qiagen, Valencia, Calif.). The obtained DNA fragments were digested with Sac I and Hind III, respectively, cleaned by using a QIAquick Nucleotide Removal Kit (Qiagen) and ligated into pBAD/His B (linearized by Sac I and Hind III before being used for ligation). About 300 ng of the insert and 50 ng of digested pBAD/His B were incubated with 3 units of T4 DNA ligase (Promega, Madison, Wis.) at 16° C. overnight. Half (5 µl) of the ligation mixture was transformed into Top10™ competent Escherichia coli cells.

Plasmids containing inserts were identified by digestion with Sac I and Hind III. Plasmids were then sequenced and those with the correct sequences were used for protein expression.

Induction of Protein Expression

To express GBP3.1-EGFP and C6-EGFP, 50 µl of overnight cultures of Top10 cells transformed with the plasmids pBADB-GBP3.1 EFGP or pBADB-C6EGFP were added to 50 ml of low salt LB medium containing ampicillin (100 µg/ml) in a 500 ml flask and shaken in an orbital shaker at 250 rpm (37° C.) until the OD$_{450}$ reached 0.4-0.5 (about 5-6 hours). L-(+)-arabinose (Sigma, St. Louis, Mo.) was then added to the culture to induce protein expression (final concentration of arabinose was 0.02%). Protein expression was continued overnight at 30° C. with rotation at 250 rpm. The overnight cell cultures were chilled at 4° C. for 15 min and the cells were then transferred into a 50 ml centrifuge tube (Fisher Scientific, Waltham, Mass.) and harvested by centrifugation in a swinging bucket rotor at 4000 g for 25 mins. The cell pellets were frozen at −80° C. for at least 30 min before being used for protein purification.

Purification of 6×His-Tagged Proteins by Ni-NTA Column

His-tagged proteins were purified using Ni-NTA (nickel-nitrilotriacetate) agarose resin (Qiagen) according to the manufacturer's instructions. The purification was under native conditions, and a batch purification method was used. All the steps for the protein purification were performed either on ice or at 4° C.

The harvested bacterial pellets were resuspended in 5 ml of lysis buffer and sonicated on ice. The sonicated resuspensions were transferred to 1.5 ml tubes and centrifuged (rcf 1000×g) in a bench-top centrifuge for 5 min at 4° C. Supernatants were mixed with 1 ml of Ni-NTA resin in a 15 ml centrifuge tube (Fisher Scientific) and incubated by rotating at 4° C. for 2 hrs before being loaded into a 1 ml Polypropylene Column (Qiagen). The column was washed with 4×5 ml washing buffer and eluted with 3 ml of elution buffer. Elution was collected in 500 µl fractions. 20 µl of each fraction was checked by separation in a 12% SDS-polyacrylamide gel.

Fractions containing the fusion proteins were stored at −80° C. As needed, the purified proteins were concentrated by YM-3 Centricon Centrifugal Filter Devices (Amicon, Beverly, Mass.) and dialyzed in Side-A-Lyzer Dialysis Cassettes (0.1-0.5 ml capacity and 3,500 MWCO) (Pierce Chemical Co., Rockford, Ill.) with PBS buffer.

The use of the EFGP allowed visualization of fusion proteins in the aphids upon exposure to ultraviolet light.

GBP3.1-EGFP and the control construct C6-EGFP were expressed in *E. coli* with 6×His tags and purified.

Figure 4:
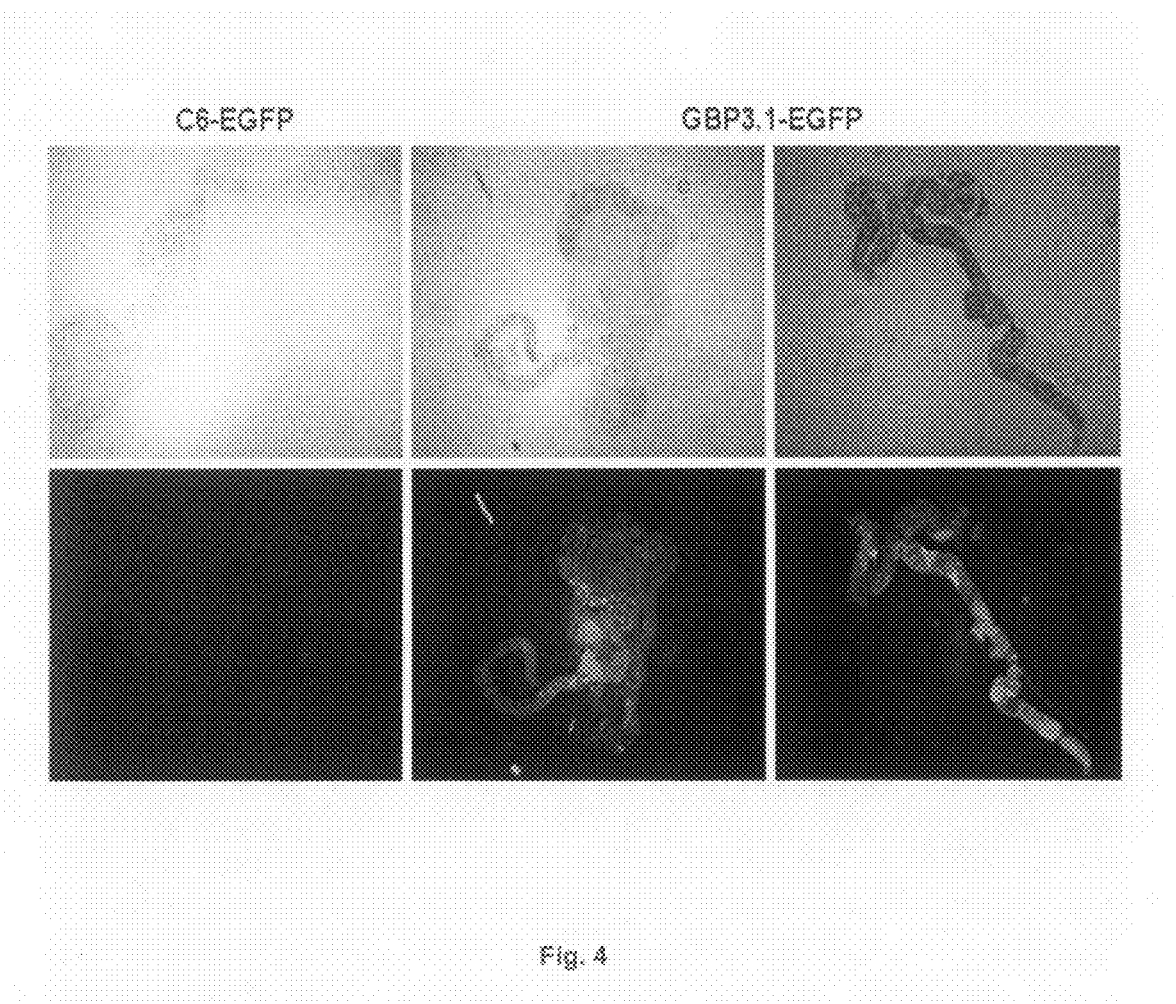
FIG. 4 demonstrates that GBP3.1-EGFP binds to the aphid gut. Pea aphids were fed with either C6-EGFP (negative control) or GBP3.1-EGFP overnight. Aphid guts were dissected and observed with normal (visible light) illumination (top panel) and with ultraviolet light illumination (bottom panel) to observe fluorescence. Fluorescence was observed only in aphids fed with the GBP3.1-EGFP protein.

EGFP, GBP3.1-EGFP or C6-EGFP was fed to pea aphids by membrane feeding (Chay et al., 1996, supra). In contrast to the two control treatments where only background fluorescence was apparent, areas of fluorescence were seen in aphids that ingested GBP3.1-EGFP. Aphid guts were dissected and observed under normal light (top panel) and under UV light to observe fluorescence (FIG. 4, bottom panel). Fluorescence was only detected in aphids fed with GBP3.1-EGFP.

Fluorescence was localized to the gut of aphids that fed on GBP3.1-EGFP. These results indicate that following feeding the majority of GBP3.1-EGFP either bound to the gut surface or entered the gut cells, but did not appear to enter the hemocoel (body cavity) of the aphid. The results are depicted in FIG. 4.

Figure 5:
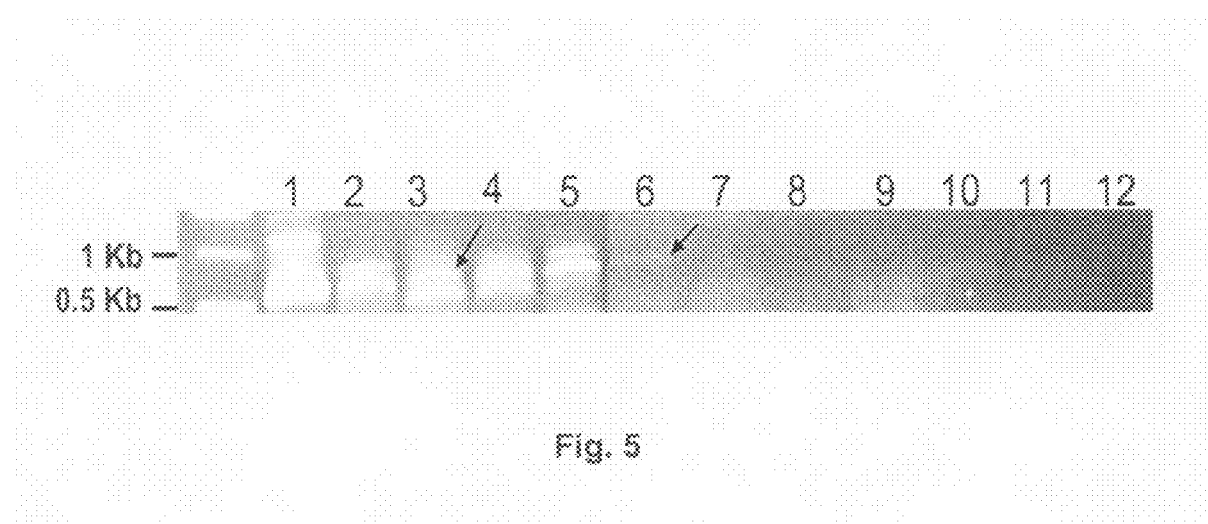
FIG. 5 illustrates the detection of PEMV RNA in hemolymph from aphids fed on C6-EGFP or GBP3.1-EGFP before feeding on PEMV infected plants. Each sample contains the RNA from 5 aphids. The expected size of the DNA fragment generated by RT-PCR is 607 bp (arrow), corresponding to nt 4123-4729 of wild type RNA1. Lane 1. Positive control for PCR: cloned RNA1 template; Lanes 2-5, samples from aphids fed on C6-EGFP overnight before feeding on PEMV infected plants for 30 min.; Lanes 6-11 samples from aphids fed on GBP3.1-EGFP overnight before feeding on PEMV infected plants for 60-90 min. Lane 12, control aphids (no virus).

We have shown that the phage that expresses GBP3.1 (the peptide which inhibits the binding of PEMV to the aphid gut, peptide of the sequence set forth in SEQ ID NO:1), displayed by phage PhD3.1, was able to delay or block PEMV movement from the gut into the aphid hemocoel, while a phage expressing a non-relevant peptide (C6; SEQ ID NO:22) did not. A similar experiment was carried out using the fusion protein GBP3.1-EGFP rather than the phage that expresses and displays the GBP3.1 peptide. GBP3.1-EGFP or C6-EGFP (fusion protein with control, non-binding peptide sequence having the sequence set forth in SEQ ID NO:22) was fed to pea aphids, and then the aphids were moved to PEMV infected plants to test whether the peptide fusion proteins blocked virus penetration. It had been shown previously that it takes 20-30 min for PEMV to accumulate to a detectable level in the hemocoel following the onset of virus acquisition. The aphids were fed C6-EGFP or GBP3.1-EGFP overnight (>16 hours), and then the aphids were transferred to plants infected with wild type PEMV. Aphids fed on C6-EGFP were allowed to feed on the infected plants for 30 min, while aphids fed on GBP3.1-EGFP were allowed to feed on infected plants for 60 to 90 min. To avoid feeding aphids on plants with different levels of PEMV infection, the same plants were used for viral acquisition for both C6-EGFP—and GBP3.1-EGFP-fed aphids. Following virus acquisition, hemolymph was isolated from the aphids, and RNA was extracted. The RNA samples were used for RT-PCR for detection of PEMV RNA (FIG. 5). PEMV RNA was detected from the hemolymph of all samples derived from C6-EGFP fed aphids (Lane 2-5), but only from one sample from GBP3.1-EGFP fed aphids (lane 6). This result supports the hypothesis that GBP3.1 binds to the PEMV receptor, thereby hindering uptake of PEMV into the aphid hemocoel. The single positive result (lane 6) may be due to inefficient membrane feeding of aphids on GBP3.1-EGFP in that case.

Example 5

Plant Transformation

Additional embodiments of the invention relate to transformed seeds and transgenic progeny plants of the parent transgenic plant, all expressing the gut-binding-peptide, peptide multimer or a fusion protein comprising same, advantageously expressed in the phloem of the plants, and the use of said plants, seeds, and plant parts in agro-industry and/or horticulture and/or in the production of food, feed, industrial products, oil, nutrients, and other valuable products. These other embodiments of the invention relate to transformed seed of such a plant, methods for breeding other plants using said plant, use of said plant in breeding or agriculture, and use of said plant to produce chemicals, food or feed products, as well as to reduce transmission of targeted virus diseases spread by sap-sucking insects and to reduce plant damage and economic losses due to those targeted virus diseases. The expression of the gut-binding peptide, peptide multimer or a fusion protein comprising same reduces the spread of viruses carried by sap-sucking insects, luteoviruses, geminiviruses and especially enamoviruses such as Pea enation mosaic virus carried by aphids, and as a result, the infection of plants by such viruses is reduced and crops expressing the peptide, peptide multimer or fusion protein are afforded some level of protection against damage due to such viral infection. The use of transgenic plants expressing the peptide, peptide multimer or fusion protein among, near or surrounding a nontransgenic plant of interest also affords some protection to the nontransgenic plant of interest.

For recombinant production of the peptide in a host organism, the gut binding, plant virus inhibiting inhibiting peptide coding sequence is inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the one ordinarily skilled in the art. The resultant molecule, containing the individual elements linked in proper orientation and reading frame, may be inserted into a vector capable of being transformed into the host cell. Suitable expression vectors and methods for recombinant production of proteins are well known for host organisms such as *E. coli* (see, e.g. Studier and Moffatt. 1986. J. Mol. Biol. 189: 113; Brosius. 1989. DNA 8: 759), yeast (see, e.g., Schneider and Guarente. 1991. Meth. Enzymol. 194: 373) and insect cells (see, e.g. Luckow and Summers. 1988. Bio/Technol. 6: 47). Specific examples include plasmids such as pBluescript (Stratagene, La Jolla, Calif.), pFLAG (International Biotechnologies, Inc., New Haven, Conn.), pTrcHis (Invitrogen, Carlsbad, Calif.).

Plants expressing a peptide of the invention can be obtained by stably transforming a peptide coding sequence of the present invention into a plant cell such that it is expressed in the above-ground plant tissues, and preferably in phloem, and is stably maintained in the plant.

Transgenic Pea Plants that Block PEMV Transmission

For expression in planta, the peptide GBP3.1 (SEQ ID NO:9) or a peptide whose sequence conforms to consensus sequence SEQ ID NO:29 can be expressed either alone (as an individual peptide or as a multimer of the peptide sequence; tandem repeat, 2 to 10 copies) or fused to a protein. The multiple copies may be separated by a spacer sequence, such as (but not limited to) the proline-rich portion of a luteovirus coat protein read-through domain, for example the PEMV 1 amino acid sequence: GDDAPPSPGPDPGPQPPPPP-PPSPTPVG (SEQ ID NO: 8) encoded by the nucleotide sequence: tgagggga cgacgctccc ccgtcaccag ggcctgatcc cggcccccaa ccaccaccac ctccaccccc aagtccsact cccgtagga (SEQ ID NO: 16) (Genbank accession no. Y09099) or by a synonymous nucleotide sequence. Advantageously, the gene for the fusion enhances the efficiency of blocking virus entry into the hemocoel of the aphid by either interfering with the target virus replication in the transgenic plant (e.g. a plant virus coat protein), or providing resistance to the aphid infestation (e.g. mannose-binding lectin such as garlic leaf lectin, *Allium sativum* agglutinin, ASA). The PEMV coat protein (CP), garlic leaf lectin and reporter gene (e.g. EGFP) fusions are useful.

As specifically exemplified herein, the plant used for transgenic expression of GBP3.1 is pea (*Pisum sativum* ssp.). Other dicotyledonous species, especially legumes, can be similarly constructed. Monocots susceptible to attack by aphids and viruses can also be made.

*Agrobacterium tumefaciens*-mediated transformation is used to make PEMV-resistant pea plants. T-DNA binary vectors are used for introducing the plant-expressible sequences encoding a gut binding peptide, peptide multimer or fusion protein of the present invention. Embryonic segments from mature pea seeds are used as initial explants. Alternatively, stem segment and axillary buds may also used; see Krejci et al., 2007. The transformation of pea (*Pisum sativum* L.): applicable methods of *Agrobacterium tumefaciens*-mediated gene transfer. Acta Physiol. Plant. 29:157-163, which provides methods for preparing and transforming embryonic segments, and for regeneration of transformant plants from the callus tissue. See also Jordan et al. 1993. Evaluation of a cotyledonary node regeneration system for *Agrobacterium*-mediated transformation of pea (*Pisum sativum* L.). In Vitro Cell Dev. Biol. 29:77-82.

Figure 6:
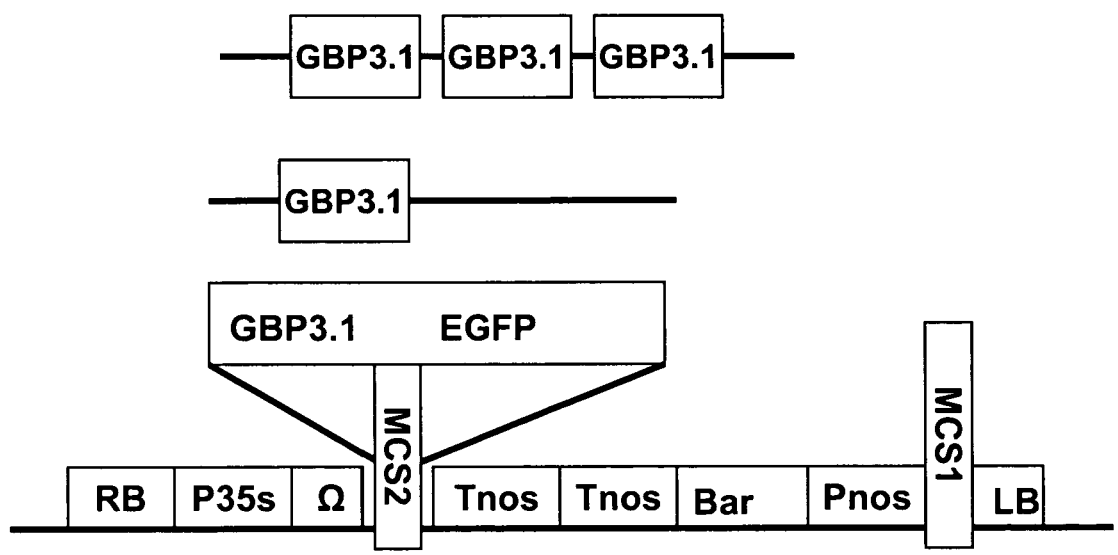
FIG. 6 illustrates the strategy for expression of a GBP3.1 peptide, peptide multimer or GBP3.1-containing fusion protein. The target coding sequences are cloned into multiple cloning site 2 (MCS2). P35s: promoter; Ω: expression enhancer; Tnos: Nos terminator; Bar: Bar gene, coding the phosphinothricin acetyltransferase (PAT) that confers resistance to the herbicide phosphinothricin (PPT) for selection of transformed plants. RB and LB: right and left T-DNA borders for inserting the expression cassette into the plant genome.

The strategy for construction of the vectors is summarized in FIG. 6. See also Xiao et al., 1999. A mini binary vector series for plant transformation. Plant Molecular Biology 40: 711-717.

PCR is used to confirm that the transgenic plants contain the proper insertion of the target gene. RT-PCR is used to confirm that the peptide, tandem repeat or fusion protein mRNA is transcribed, and ELISA or western blots establish that the protein is expressed.

The effectiveness of the expressed peptide, peptide multimer or fusion protein is shown by bioassay of the transformed plants. For virus transmission blocking tests, the transformants are inoculated with PEMV and fed to pea aphids (*Acyrthosiphon pisum*) for 48 hours. The aphids are then transferred to healthy transformed plants for inoculation for 48 hours. The plants are subsequently tested for infection with PEMV.

Examples of constitutive promoters which function in plant cells include the Cauliflower mosaic virus (CaMV) 19S or 35S promoters, CaMV 35S double or enhanced promoters, the 35S promoter and an enhanced or double 35S promoter such as that described in Kay et al., Science 236: 1299-1302 (1987); nopaline synthase promoter; the rice actin promoter (McElroy et al. 1991. Mol. Gen. Genet. 231: 150), maize ubiquitin promoter (EP 0 342 926; Taylor et al. 1993. Plant Cell Rep. 12: 491), and the Pr-1 promoter from tobacco, *Arabidopsis*, or maize (see U.S. Pat. No. 5,614,395), the Peanut chlorotic streak caulimovirus (PCISV) promoter (U.S. Pat. No. 5,850,019), the 35S promoter from Cauliflower mosaic virus (CaMV) (Odell et al. 1985. Nature 313:810-812), promoters of *Chlorella* virus methyltransferase genes (U.S. Pat. No. 5,563,328), the full-length transcript promoter from Figwort mosaic virus (FMV) (U.S. Pat. No. 5,378,619); the promoters from such genes as rice actin (McElroy et al. 1990. Plant Cell 2:163-171), ubiquitin (Christensen et al. 1989. Plant Mol. Biol. 12:619-632) and Christensen et al. 1992. Plant Mol. Biol. 18:675-689), pEMU (Last et al. 1991. Theor. Appl. Genet. 81:581-588), MAS (Velten et al. 1984. EMBO J. 3:2723-2730), maize H3 histone (Lepetit et al. 1992. Mol. Gen. Genet. 231:276-285 and Atanassova et al. 1992. Plant Journal 2:291-300), *Brassica napus* ALS3 (WO 97/41228); and promoters of various *Agrobacterium* genes (see, e.g., U.S. Pat. Nos. 4,771,002, 5,102,796, 5,182,200 and 5,428,147). Light-regulated promoters suitable for expression in above-ground tissues include the small subunit of ribulose bisphosphate carboxylase (ssuRUBISCO) promoter and the like. The promoters themselves may be modified to manipulate promoter strength to increase peptide, peptide multimer or fusion protein expression, in accordance with art-recognized procedures.

Guidance for the design of promoters is provided by studies of promoter structure, such as that of Harley and Reynolds. (1987). *Nucleic Acids Res.* 15:2343-2361. Also, the location of the promoter relative to the transcription start may be optimized. See, e.g., Roberts, et al. (1979) *Proc. Natl. Acad. Sci. USA* 76:760-4. Many suitable promoters for use in plants are well known in the art.

The promoter may include or be modified to include one or more enhancer elements. Promoters with enhancer elements provide for higher levels of transcription as compared to promoters without them. Suitable enhancer elements for use in plants include the PCISV enhancer element (U.S. Pat. No. 5,850,019), the CaMV 35S enhancer element (U.S. Pat. Nos. 5,106,739 and 5,164,316) and the FMV enhancer element (Maiti et al. (1997). Transgenic Res. 6:143-156). See also WO 96/23898 and Enhancers and Eukaryotic Expression (Cold Spring Harbor Press, Cold Spring Harbor, N.Y., 1983).

A 5' untranslated sequence is also employed. The 5' untranslated sequence is the portion of an mRNA which extends from the 5' cap site to the translation initiation codon. This region of the mRNA is necessary for translation initiation in plants and plays a role in the regulation of gene expression. Suitable 5' untranslated regions for use in plants include those of Alfalfa mosaic virus, Cucumber mosaic virus coat protein gene, and Tobacco mosaic virus.

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include those of the Cauliflower mosaic virus 35S gene, the phaseolin seed storage protein gene, the pea ribulose bisphosphate carboxylase small subunit E9 gene, the soybean 7S storage protein genes, the octopine synthase gene, and the nopaline synthase gene.

The peptide, peptide multimer or gut binding-inhibiting fusion protein coding sequence of the present invention is advantageously expressed in the phloem of the plant. It is then consumed by a sap-sucking insect, in which transmission of a relevant virus from plant to plant is inhibited or prevented. The CaMV 35C promoter is a useful promoter for phloem expression.

Chimeric DNA construct(s) (non-naturally occurring nucleic acid molecules) of the invention may contain multiple copies of a promoter or multiple copies of the peptide coding sequence of the present invention. In addition, the construct(s) may include coding sequences for selectable or detectable markers, each in proper reading frame with the other functional elements in the DNA molecule. The preparation of such constructs is within the ordinary level of skill in the art.

The DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the DNA sequence encoding the peptide of the invention competitive epitope containing peptide. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform any type of plant cells (see below). A genetic marker can be used for selecting transformed plant cells (a selection marker). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant expression control signals, confers resistance to kanamycin (Fraley et al. (1983) *Proc. Natl. Acad. Sci. USA* 80:4803). Another commonly used selectable marker gene is the hygromycin phosphotransferase gene which confers resistance to the antibiotic hygromycin. Vanden Elzen et al. (1995) *Plant Mol. Biol.* 5:299). Additional selectable marker genes of bacterial origin that confer resistance to antibiotics include gentamicin acetyl transferase, streptomycin phosphotransferase, aminoglycoside-3'-adenyl transferase, the phosphinothricin acetyltransferase conferring resistance to the herbicide phosphinothricin, and the bleomycin resistance determinant (Hayford et al. (1988) *Plant Physiol.* 86:1216; Jones et al. (1987). *Mol. Gen. Genet.* 210:86; Svab et al. (1990) *Plant Mol. Bio.* 14:197; Hille et al. (1986) *Plant Mol. Biol.* 7:171). Other selectable marker genes confer resistance to herbicides such as glyphosate, glufosinate or bromoxynil (Comai et al. (1985) *Nature* 317:741-744; Stalker et al. (1988) *Science* 242:419-423; Hinchee et al. (1988) *Bio/Technology* 6:915-922; Stalker et al. (1988) *J. Biol. Chem.* 263: 6310-6314; Gordon-Kamm et al. (1990) *Plant Cell* 2:603-618).

Other selectable markers useful for plant transformation include, without limitation, mouse dihydrofolate reductase, plant 5-enolpyruvylshikimate-3-phosphate synthase, and plant acetolactate synthase (Eichholtz et al. (1987) *Somatic Cell Mol. Genet.* 13:67; Shah et al. (1986) *Science* 233:478; Charest et al. (1990) *Plant Cell Rep.* 8:643; EP 154,204.

Commonly used genes for screening presumptively transformed cells include but are not limited to β-glucuronidase (GUS), β-galactosidase, luciferase, and chloramphenicol acetyltransferase (Jefferson, R. A. (1987) *Plant Mol. Biol. Rep.* 5:387; Teeri et al. (1989) *EMBO J.* 8:343; Koncz et al. (1987) *Proc. Natl. Acad. Sci. USA* 84:131; De Block et al. (1984) *EMBO J.* 3:1681), green fluorescent protein (GFP) (Chalfie et al. (1994) *Science* 263:802; Haseloff et al. (1995) *TIG* 11:328-329 and PCT application WO 97/41228). Another approach to the identification of relatively rare transformation events has been use of a gene that encodes a dominant constitutive regulator of the *Zea mays* anthocyanin pigmentation pathway (Ludwig et al. 1990. Science 247:449). To select cells which have successfully undergone transformation, it is preferred to introduce a selectable marker which confers, to the cells which have successfully undergone transformation, a resistance to a biocide (for example a herbicide), a metabolism inhibitor such as 2-deoxyglucose-6-phosphate (WO 98/45456) or an antibiotic. The selection marker permits the transformed cells to be selected from untransformed cells (McCormick et al. (1986) *Plant Cell Reports* 5:81-84). Suitable selection markers are described above and include antibiotic resistance markers, among others.

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selectable markers used routinely in transformation include the nptII gene which confers resistance to kanamycin and related antibiotics (Messing and Vierra. (1982) *Gene* 19: 259-268; Bevan et al. (1983). *Nature* 304: 184-187), the bar gene which confers resistance to the herbicide phosphinothricin (White et al. (1990) *Nucl Acids Res* 18: 1062; Spencer et al. (1990) *Theor Appl Genet.* 79: 625-631), the hph gene which confers resistance to the antibiotic hygromycin (Blochinger and Diggelmann. (1984) *Mol Cell Biol* 4: 2929-2931), and the dhfr gene, which confers resistance to methotrexate (Bourouis et al. (1983). *EMBO J.* 2(7): 1099-1104).

Many vectors are available for transformation using *A. tumefaciens*. These typically carry at least one T-DNA border sequence and include vectors such as pBIN19 (Bevan. 1984. Nucl. Acids Res.). Below the construction of two typical vectors is described. pCAMBIA and other vectors are well known to the art as well.

The exemplary binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. 1987. Gene 53: 153-161. Various derivatives of pCIB10 have been constructed which incorporate the gene for hygromycin B phosphotransferase described by Gritz et al. (1983). Gene 25: 179-188). These derivatives enable selection of transgenic plant cells on hygromycin only (pCIB743), or hygromycin and kanamycin (pCIB715, pCIB717). See, e.g., Rogers et al., *Methods for Plant Molecular Biology, Weissbach and Weissbach*, eds, Academic Press, San Diego, Calif., 1988, for a description of a kanamycin resistance marker. Other selective agents for use in plants include bleomycin, gentamicin and certain herbicide resistance markers.

Transformation without the use of *A. tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed.

Gene sequences intended for expression in transgenic plants are first assembled in expression cassettes behind a suitable promoter and upstream of a suitable transcription terminator. These expression cassettes can then be easily transferred to the plant transformation vectors of choice.

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase (nos) terminator, the pea rbcS E9 terminator. These can be used in both monocotyledonous and dicotyledonous plants.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene significantly enhance the expression of the wild-type gene under its cognate promoter when introduced into maize cells. Intron 1 enhances expression in fusion constructs with the chloramphenicol acetyltransferase gene (Callis et al. (1987) *Genes Develop.* 1: 1183-1200). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses also enhance expression, especially in dicotyledonous cells. Leader sequences from Tobacco mosaic virus (TMV, the "W-sequence"), Maize chlorotic mottle virus (MCMV), and Alfalfa mosaic virus (AMV) have been shown to enhance expression (e.g. Gallie et al. (1987) *Nucl. Acids Res.* 15: 8693-8711; Skuzeski et al. (1990) *Plant Molec. Biol.* 15:65-79).

*Agrobacterium*-mediated transformation is a preferred technique for transformation of dicots because of the high efficiency of transformation and success with many different species. The many crop species which are routinely transformable by *Agrobacterium* include tobacco, tomato, sunflower, cotton, oilseed rape, potato, soybean, peas, beans, alfalfa and poplar (EP 317 511, cotton; EP 0 249 432, tomato, to Calgene; WO 87/07299, *Brassica*, to Calgene; U.S. Pat. No. 4,795,855, poplar). *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. (1993) *Plant Cell* 5: 159-169). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen and Willmitzer. (1988) *Nucl. Acids Res.* 16: 9877).

Once an expression construct or expression vector of the invention has been established, it can be transformed into a plant cell. A variety of methods for introducing nucleic acid sequences (e.g., vectors) into the genome of plants and for the regeneration of plants from plant tissues or plant cells are known (*Plant Molecular Biology and Biotechnology* (CRC Press, Boca Raton, Fla., pp. 71-119 (1993); White FF. (1993) Vectors for Gene Transfer in Higher Plants; in: *Transgenic Plants*, vol. 1, Engineering and Utilization, Ed.: Kung and Wu R, Academic Press, 15-38; Jenes et al. (1993) Techniques for Gene Transfer, in: *Transgenic Plants*, vol. 1, Engineering and Utilization, Ed.: Kung and R. Wu, Academic Press, pp. 128-143; Potrykus et al. (1991) *Annu. Rev. Plant Physiol. Plant Molec. Biol.* 42:205-225; Halford and Shewry. 2000. Br. Med. Bull. 56:62-73).

Transformation methods may include direct and indirect methods of transformation. Suitable direct methods include polyethylene glycol induced DNA uptake, liposome-mediated transformation (U.S. Pat. No. 4,536,475), biolistic methods using the gene gun (particle bombardment; Fromm et al. (1990) *Bio/Technology.* 8:833-9; Gordon-Kamm et al. (1990) *Plant Cell* 2:603), electroporation, incubation of dry embryos in DNA-comprising solution, and microinjection. In the case of these direct transformation methods, the plasmid used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 116,718), viral infection by means of viral vectors (EP 067,553; U.S. Pat. No. 4,407,956; WO 95/34668; WO 93/03161) or by means of pollen (EP 270,356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) *Science* 225:1229f. The *Agrobacterium*-mediated transformation is best suited to dicotyledonous plants but has also been adapted to monocotyledonous plants. The transformation of plants by *Agrobacteria* is described, for example, in White FF, Vectors for Gene Transfer in Higher Plants; in *Transgenic Plants*, Vol. 1, Engineering and Utilization, edited by S. D. Kung and R. Wu, Academic Press, (1993), pp. 15-38; Jenes B et al. (1993) Techniques for Gene Transfer, in: *Transgenic Plants*, Vol. 1, Engineering and Utilization, edited by S. D. Kung and R. Wu, Academic Press, pp. 128-143; Potrykus (1991). *Annu Rev Plant Physiol Plant Molec Biol* 42:205-225).

Transformation may result in transient or stable transformation and expression; stable transformation is preferred in the practice of the present invention. Although a nucleotide sequence of the present invention can be inserted into any plant and plant cell, it is particularly useful in crop plant cells.

Various tissues are suitable as starting material (explant) for the *Agrobacterium*-mediated transformation process including but not limited to callus (U.S. Pat. No. 5,591,616; EP 604 662), immature embryos (EP 672 752), pollen (U.S. Pat. No. 5,929,300), shoot apex (U.S. Pat. No. 5,164,310), or in planta transformation (U.S. Pat. No. 5,994,624). The method and material described herein can be combined with virtually all *Agrobacterium* mediated transformation methods known in the art. Preferred combinations include, but are not limited, to the following starting materials and methods: monocotyledonous plants: EP-A1672 752, EP-A1604 662, U.S. Pat. No. 6,074,877, U.S. Pat. No. 6,037,522, WO 01/12828; banana, U.S. Pat. No. 5,792,935; EP 731 632; U.S. Pat. No. 6,133,035; barley, WO 99/04618; maize, U.S. Pat. No. 5,177,010; U.S. Pat. No. 5,987,840; pineapple, U.S. Pat. No. 5,952,543; WO 01/33943; soybean, U.S. Pat. No. 5,376, 543; EP 397 687; U.S. Pat. No. 5,416,011; U.S. Pat. No. 5,968,830; U.S. Pat. No. 5,563,055; U.S. Pat. No. 5,959,179; EP 652 965; EP 1,141,346; brassicacious plants, U.S. Pat. No. 5,188,958; EP 270 615; EP-A1 1,009,845; beans, U.S. Pat. No. 5,169,770; EP 397 687; peas, U.S. Pat. No. 5,286,635; cotton, U.S. Pat. No. 5,004,863; EP-A1 270 355; U.S. Pat. No. 5,846,797; EP-A1 1,183,377; EP-A1 1,050,334; EP-A1 1,197,579; EP-A1 1,159,436, U.S. Pat. No. 5,929,300, U.S. Pat. No. 5,994,624, and tomato, U.S. Pat. No. 5,565,347, and other plants and methods are also known to the art.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (ie. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. (1986) *Biotechnology* 4:1093-1096). EP 0 292 435, EP 0 392 225 and WO 93107278 describe techniques for the preparation of callus and protoplasts from an elite inbred line of maize, transformation of protoplasts using PEG or electroporation, and the regeneration of maize plants from transformed protoplasts. Gordon-Kamm et al. (1990) *Plant Cell* 2: 603-618 and Fromm et al. (1990) *Biotechnology* 8: 833-839 have published techniques for transformation of A188-derived maize line using particle bombardment. Furthermore, WO 93/07278 and Koziel et al. (1993) *Biotechnology* 11: 194-200 describe techniques for the transformation of elite inbred lines of maize by particle bombardment. This technique utilizes immature maize embryos of 1.5-2.5 mm length excised from a maize ear 14-15 days after pollination and a biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. (1988) *Plant Cell Rep* 7:379-384; Shimamoto et al. (1989) *Nature* 338: 274-277; Datta et al. (1990) *Biotechnology* 8: 736-740). Both types are also routinely transformable using particle bombardment (Christou et al. (1991) *Biotechnology* 9: 957-962).

Transgenic plants can be regenerated in the known manner from the transformed cells. The resulting plantlets can be planted and grown in the customary manner. Preferably, two or more generations should be cultured to ensure that the genomic integration is stable and hereditary. Suitable methods are described (Fennell et al. (1992) *Plant Cell Rep.* 11: 567-570; Stoeger et al. (1995) *Plant Cell Rep.* 14:273-278; Jahne et al. (1994) *Theor Appl Genet.* 89:525-533).

EP 332 581 describes techniques for the generation, transformation and regeneration of Pooideae protoplasts. These techniques allow the transformation of *Dactylis* and wheat. Furthermore, wheat transformation was been described by Vasil et al. (1992) *Biotechnology* 10: 667-674) using particle bombardment into cells of type C long-term regenerable callus, and also by Vasil et al. (1993) *Biotechnology* 11: 1553-1558 and Weeks et al. (1993) *Plant Physiol.* 102: 1077-1084 using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige and Skoog. (1962) *Physiologia Plantarum* 15: 473-497) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of .about.1000 psi using a standard 80 mesh screen. After bombardment, the embryos are placed back into the dark to recover for about 24 h (still on osmoticum). After 24 hrs, the embryos are removed from the osmoticum and placed back onto induction. medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. U.S. patent application Ser. No. 08/147,161 describes methods for wheat transformation.

Expression directed by a particular sequence means there is transcription and translation of an associated downstream sequence. With reference to tissue-specific regulation of expression of a peptide sequence of interest operably linked to the plant-expressible transcription regulatory sequence, expression may be advantageously determined by a strong constitutive promoter such as the Cauliflower Mosaic Virus 19S or 35 S promoter, a tandem repeat 35S promoter, the actin 2 promoter from *Arabidopsis thaliana*, among others, or advantageously, a phloem-specific promoter.

Transformation to provide transgenic plants expressing a peptide of the invention can be carried out by art-known methods. A vector construct carrying a nucleotide sequence encoding a peptide of the invention such as PhD3.1 (SEQ ID NO:9) will optionally include DNA encoding a signal peptide to provide for export of the peptide from the transformed cell and a suitable plant promoter. A phloem-specific promoter is preferred, allowing expression to be maximized in phloem tissue (see, e.g. Booker, J. et al. (2003) Plant Cell 15(2):495-507; Jones, J. D. et al. (1992) *Transgenic Res.* 1(6):285-297; Truenit, E. et al. (1995) Planta 196(3):564-570). However, a highly active promoter, such as CaMV 35S promoter can also be used. Given the small size of peptides of the invention, the expression level can be increased by including multiple copies of the same peptide controlled by a single promoter (see, e.g. Marcos J. F. et al. (1994) *Plant Mol. Biol.* 24:495-503; Beck von Bodman, S. et al. (1995) *Bio/technology* 13:587-591).

Transformation can be carried out by a variety of known methods. Commercial facilities for carrying out plant transformation are available, e.g., at the Iowa State University, Plant Transformation Facility, Ames Iowa, and techniques for transformation are well known and widely accessible in the art. Suitable transformants are identified or selected by means known in the art. Those skilled in the art can make appropriate choices from known methods transformation, selection and regeneration based on the plant species to be transformed. The choice of plant species will be determined by the virus whose inhibition is desired.

Selected transformants are regenerated using art-known methods appropriate for the desired plant species. For pea (*Pisum sativum*) see, e.g. Nauerby, B. et al. (1991) *Plant Cell Reports* 676-679.

All references and patent documents cited herein reflect the level of skill in the relevant arts and are incorporated by reference in their entireties to the extent there is no inconsistency with the present disclosure.

The examples provided herein are for illustrative purposes and are not intended to limit the scope of the invention as claimed. Any variations in the exemplified compositions, plants and methods which occur to the skilled artisan are intended to fall within the scope of the present invention.

The invention claimed is:

1. A peptide, peptide multimer or fusion protein comprising an amino acid sequence conforming to consensus sequence: $Xaa_1$-$Xaa_2$-Cys-Ser-Lys-Lys-Tyr-Pro-$Xaa_3$-Ser-$Xaa_4$-Cys-$Xaa_5$-$Xaa_6$, wherein $Xaa_1$ and $Xaa_6$, independently of one another, can be any amino acid or no amino acid; $Xaa_2$ is Thr or Gly; $Xaa_3$ is Arg or Ser; $Xaa_4$ is Asp or Glu or Pro; and $Xaa_5$ is Met or Gln (SEQ ID NO:29).

2. The peptide, peptide multimer or fusion protein of claim 1 comprising an amino acid sequence selected from the group SEQ ID NO:1, SEQ ID NO:2, SEQ ID NO:3, SEQ ID NO:4, SEQ ID NO:5, SEQ ID NO; 6, SEQ ID NO:7, SEQ ID NO:9, SEQ ID NO:10, SEQ ID NO:11, SEQ ID NO:12, SEQ ID NO:13, SEQ ID NO:14 and SEQ ID NO:15.

3. A DNA segment encoding a peptide, peptide multimer or fusion protein of claim 1.

4. A DNA segment encoding a peptide, peptide multimer or fusion protein of claim 2.

5. A DNA segment according to claim 4, encoding the peptide, peptide multimer or fusion protein comprising the amino acid sequence of SEQ ID NO:9.

6. A DNA segment according to claim 5, comprising the sequence of SEQ ID NO:17.

7. A transformed plant containing and expressing a DNA segment according to claim 3.

8. A transformed pea plant according to claim 7, wherein the peptide, peptide multimer or fusion protein is expressed in phloem tissue of the plant.

9. A method of inhibiting entry of a target virus ingested by an insect selected from the group consisting of aphid, planthopper, thrips and whitefly, into the hemocoel of said insect, comprising
    providing a peptide, peptide multimer or fusion protein that inhibits binding of the virus to the insect gut, wherein said peptide, peptide multimer or fusion protein comprises the sequence of SEQ ID NO:29; and
    bringing a source of food comprising the peptide, peptide multimer or fusion protein into contact with the insect under conditions that allow the insect to ingest the food, whereby the peptide, peptide multimer or fusion protein ingested by the insect inhibits entry of any target virus ingested by the insect into the hemocoel of the insect.

10. The method of claim 9, wherein the food source is phloem tissue of a transgenic plant expressing the peptide, peptide multimer or fusion protein in phloem of the plant.

11. The method of claim 10, wherein the peptide, peptide multimer or fusion protein comprising said peptide, peptide multimer or fusion protein is selected to inhibit binding of the target virus to gut tissue of an insect that transmits said virus.

12. The method of claim 11, wherein the insect is an aphid, thrips, leafhopper or other sap-sucking insect.

13. The method of claim 12, wherein the virus is Pea enation mosaic virus and the peptide, peptide multimer or the peptide comprised within the fusion protein is one selected from the group of peptides having amino acid sequences given in SEQ ID NOS:1-7 and 9-15.

14. The method of claim 11, wherein the peptide, peptide multimer or fusion protein is ingested by the insect prior to virus ingestion.

15. The method of claim 11, wherein the peptide, peptide multimer or fusion protein comprising the peptide is ingested by the insect coincidentally with virus ingestion.

16. A method for inhibiting transmission of a virus disease of a plant, wherein said virus disease is spread from plant to plant by sap-sucking insects, comprising the step of providing a transgenic plant expressing the DNA segment of claim 3, whereby virus binding to guts of the sap-sucking insects is inhibited and transmission of the virus disease is reduced.

* * * * *

SEQUENCE LISTING

<160> NUMBER OF SEQ ID NOS: 38

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Ala Thr Cys Ser Lys Lys Tyr Pro Arg Ser Pro Cys Met Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Ala Thr Cys Ser Lys Lys Tyr Pro Ser Ser Asp Cys Gln Ala
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic construct

<400> SEQUENCE: 3

Ala Thr Cys Ser Lys Lys Tyr Pro Ser Ser Glu Cys Met Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Ala Thr Cys Ser Lys Lys Tyr Pro Arg Ser Asp Cys Met Ala

<210> SEQ ID NO 5
<211> LENGTH: 14
<212> TYPE: PRT
<213> ORGANISM: Artificial Sequence
<220> FEATURE:
<223> OTHER INFORMATION: Synthetic construct

<400> SEQUENCE: 5

Ala Thr Cys Ser Lys Lys Tyr Pro Ser Ser Pro Cys Gln Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Ala Thr Cys Ser Lys Lys Tyr Pro Arg Ser Pro Cys Gln Ala
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Ala Gly Cys Ser Lys Lys Tyr Pro Arg Ser Pro Cys Met Ala
1               5                   10

<210> SEQ ID NO 8
<211> LENGTH: 28
<212> TYPE: PRT
<213> ORGANISM: Artificial Sequence
<220> FEATURE:
<223> OTHER INFORMATION: Synthetic construct

<400> SEQUENCE: 8

Gly Asp Asp Ala Pro Pro Ser Pro Gly Pro Asp Pro Gly Pro Gln Pro
1               5                   10                  15

Pro Pro Pro Pro Pro Pro Ser Pro Thr Pro Val Gly
            20                  25

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Thr Cys Ser Lys Lys Tyr Pro Arg Ser Pro Cys Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic construct

<400> SEQUENCE: 10

Thr Cys Ser Lys Lys Tyr Pro Ser Ser Asp Cys Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic construct

<400> SEQUENCE: 11

Thr Cys Ser Lys Lys Tyr Pro Ser Ser Glu Cys Met
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Thr Cys Ser Lys Lys Tyr Pro Arg Ser Asp Cys Met
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic construct

<400> SEQUENCE: 13

Thr Cys Ser Lys Lys Tyr Pro Ser Ser Pro Cys Gln
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic construct

<400> SEQUENCE: 14

Thr Cys Ser Lys Lys Tyr Pro Arg Ser Pro Cys Gln
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic construct

<400> SEQUENCE: 15

Gly Cys Ser Lys Lys Tyr Pro Arg Ser Pro Cys Met
1               5                   10

<210> SEQ ID NO 16
<211> LENGTH: 87
<212> TYPE: DNA
<213> ORGANISM: Artificial Sequence
<220> FEATURE:
<223> OTHER INFORMATION: Synthetic construct

<400> SEQUENCE: 16

```
tgaggggacg acgctccccc gtcaccaggg cctgatcccg ggccccaacc accaccacct    60 ccaccccaa gtcccactcc cgtagga                                          87

<210> SEQ ID NO 17
<211> LENGTH: 36
<212> TYPE: DNA
<213> ORGANISM: Artificial Sequence
<220> FEATURE:
<223> OTHER INFORMATION: Synthetic construct

<400> SEQUENCE: 17
acgtgtagta agaagtatcc gcgttctccg tgtatg                               36

<210> SEQ ID NO 18
<211> LENGTH: 7
<212> TYPE: PRT
<213> ORGANISM: Artificial Sequence
<220> FEATURE:
<223> OTHER INFORMATION: Synthetic construct

<400> SEQUENCE: 18

His Asp Ser Ser Glu Asp Gln
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Gly Pro Ser Ser Asp Cys Gln
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic construct

<400> SEQUENCE: 20

Ser Ser Glu Asp Gln
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic construct

<400> SEQUENCE: 21

Ser Ser Asp Cys Gln
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

Ala Phe Cys Arg Thr Ala Asp Val Ile Asp Ala Cys Thr
```

```
<210> SEQ ID NO 23
<211> LENGTH: 38
<212> TYPE: DNA
<213> ORGANISM: Artificial Sequence
<220> FEATURE:
<223> OTHER INFORMATION: Synthetic construct

<400> SEQUENCE: 23
gccttttgtc gtacggctga tgtgattgat gcgtgtac                           38

<210> SEQ ID NO 24
<211> LENGTH: 33
<212> TYPE: DNA
<213> ORGANISM: Artificial Sequence
<220> FEATURE:
<223> OTHER INFORMATION: Synthetic construct

<400> SEQUENCE: 24
ccggagctcg gccacgtgta gtaagaagta tcc                               33

<210> SEQ ID NO 25
<211> LENGTH: 58
<212> TYPE: DNA
<213> ORGANISM: Artificial Sequence
<220> FEATURE:
<223> OTHER INFORMATION: Synthetic construct

<400> SEQUENCE: 25
gccacgtgta gtaagaagta tccgcgttct ccgtgtatgg ctgtgagcaa gggcgagg     58

<210> SEQ ID NO 26
<211> LENGTH: 34
<212> TYPE: DNA
<213> ORGANISM: Artificial Sequence
<220> FEATURE:
<223> OTHER INFORMATION: Synthetic construct

<400> SEQUENCE: 26
gcggagctcg gccttttgtc gtacggctga tgtg                              34

<210> SEQ ID NO 27
<211> LENGTH: 58
<212> TYPE: DNA
<213> ORGANISM: Artificial Sequence
<220> FEATURE:
<223> OTHER INFORMATION: Synthetic construct

<400> SEQUENCE: 27
gccttttgtc gtacggctga tgtgattgat gcgtgtacgg ctgtgagcaa gggcgagg     58

<210> SEQ ID NO 28
<211> LENGTH: 33
<212> TYPE: DNA
<213> ORGANISM: Artificial Sequence
<220> FEATURE:
<223> OTHER INFORMATION: Synthetic construct

<400> SEQUENCE: 28
caaaagcttg gttacttgta cagctcgtcc atg                               33

<210> SEQ ID NO 29
<211> LENGTH: 14
<212> TYPE: PRT
<213> ORGANISM: Artificial Sequence
```

-continued

```
<220> FEATURE:
<223> OTHER INFORMATION: Synthetic construct:  consensus sequence
      of gut-binding peptide.
<220> FEATURE:
<221> NAME/KEY: MISC_FEATURE
<222> LOCATION: (1)..(1)
<223> OTHER INFORMATION: At position 1, Xaa can be any amino acid
      or no amino acid
<220> FEATURE:
<221> NAME/KEY: MISC_FEATURE
<222> LOCATION: (2)..(2)
<223> OTHER INFORMATION: At position 2, Xaa can be Thr or Gly
<220> FEATURE:
<221> NAME/KEY: MISC_FEATURE
<222> LOCATION: (9)..(9)
<223> OTHER INFORMATION: At position 9, Xaa can be Arg or Ser
<220> FEATURE:
<221> NAME/KEY: MISC_FEATURE
<222> LOCATION: (11)..(11)
<223> OTHER INFORMATION: At position 11, Xaa can be Asp, Glu or Pro
<220> FEATURE:
<221> NAME/KEY: MISC_FEATURE
<222> LOCATION: (13)..(13)
<223> OTHER INFORMATION: At position 13, Xaa can be Gln or Met
<220> FEATURE:
<221> NAME/KEY: MISC_FEATURE
<222> LOCATION: (14)..(14)
<223> OTHER INFORMATION: At position 14, Xaa can be any amino acid
      or no amino acid

<400> SEQUENCE: 29

Xaa Xaa Cys Ser Lys Lys Tyr Pro Xaa Ser Xaa Cys Xaa Xaa
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic construct

<400> SEQUENCE: 30

Arg Ser Arg Ser Lys Ala Asn Gln Arg Arg Arg Pro Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic construct

<400> SEQUENCE: 31

Ala Asn Gln Arg Arg Arg Arg Pro Arg Arg Val Val Val Val
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic construct

<400> SEQUENCE: 32

Arg Arg Pro Arg Arg Val Val Val Val Ala Pro Ser Met Ala
1               5                   10

<210> SEQ ID NO 33
<211> LENGTH: 14
<212> TYPE: PRT
<213> ORGANISM: Artificial Sequence
```

```
<220> FEATURE:
<223> OTHER INFORMATION: Synthetic construct

<400> SEQUENCE: 33

Val Ala Pro Ser Met Ala Gln Pro Arg Thr Gln Ser Arg Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic construct

<400> SEQUENCE: 34

Arg Thr Gln Ser Arg Arg Pro Arg Arg Arg Asn Lys Arg Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic construct

<400> SEQUENCE: 35

Ala Thr Gly Thr Val Lys Phe Gly Pro Ser Ser Asp Cys Gln
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic construct

<400> SEQUENCE: 36

Thr Gly Thr Val Lys Phe Gly Pro Ser Ser Asp Cys Gln Cys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic construct

<400> SEQUENCE: 37

Ile Val Trp Leu Lys Val Val Tyr Gln Ser Glu Ala Ala Ala
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic construct

<400> SEQUENCE: 38

Val Leu Leu Asp Thr Trp Asn Ile Arg Ser Asn Gly Ser Ala
1               5                   10
```